Figure 1:
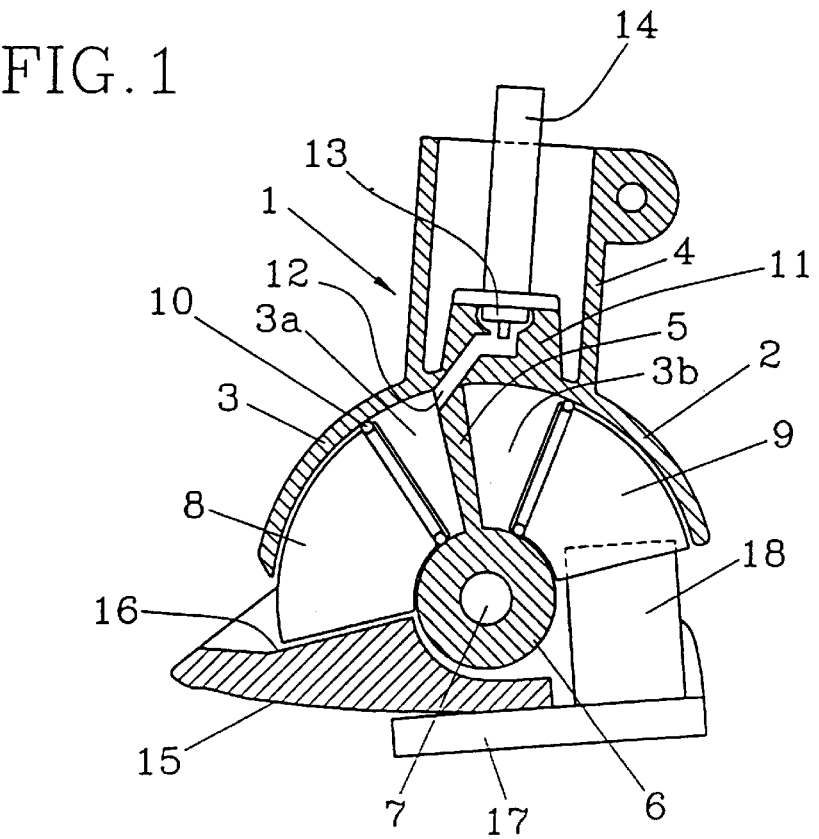

United States Patent
Gramnäs

[19]

[11] Patent Number: 5,957,981
[45] Date of Patent: Sep. 28, 1999

[54] ADJUSTABLE PROSTHESIS JOINT

[75] Inventor: Finn Gramnäs, Kinna, Sweden

[73] Assignee: Gramtec Innovation AB, Kinna, Sweden

[21] Appl. No.: 08/860,817

[22] PCT Filed: Feb. 19, 1996

[86] PCT No.: PCT/SE96/00215

§ 371 Date: Oct. 15, 1997

§ 102(e) Date: Oct. 15, 1997

[87] PCT Pub. No.: WO96/25898

PCT Pub. Date: Aug. 29, 1996

[30] Foreign Application Priority Data

Feb. 21, 1995 [SE] Sweden .................................. 9500653

[51] Int. Cl.$^6$ .................................. A61F 2/64; A61F 2/66
[52] U.S. Cl. .................................. 623/47; 623/50; 623/53
[58] Field of Search .................................. 623/21, 36, 37, 623/40, 42, 43, 44, 46, 50, 52, 55, 47

[56] References Cited

U.S. PATENT DOCUMENTS 5,704,945  1/1998  Wagner et al. ............................. 623/44

OTHER PUBLICATIONS

Mauch Laboratories, Inc., Hydraulik Ankle Unit Manual, p. 2, Mar. 1988.

*Primary Examiner*—Mickey Yu
*Assistant Examiner*—Alvin Stewart
*Attorney, Agent, or Firm*—Gardner, Carton & Douglas

[57] ABSTRACT

An adjustable prosthesis joint, such as a prosthesis ankle or a prosthesis foot, and intended primarily for causing setting of the angular relation between an attachment means (4) forming part thereof for affixing the prosthesis joint (1) to a cooperating body part, and a detail (17) being angularly displaceably connected thereto, whereby the prosthesis joint is provided with means adapted to be actuatable to permit or to prevent such angular displacement, respectively, whereby said means is constituted by two communicating chambers (3a, 3b) containing a flow medium, with a shiftable valve (13) provided between the chambers, and at least one body designed as a piston (8, 9), rotatably arranged in relation to said chambers and movably arranged therein and adapted to permit flow of flow medium between the two chambers, when the valve is open and under influence of an external shifting force being displaced in said chambers (3a, 3b) in order to alter the relative sizes thereof.

4 Claims, 5 Drawing Sheets

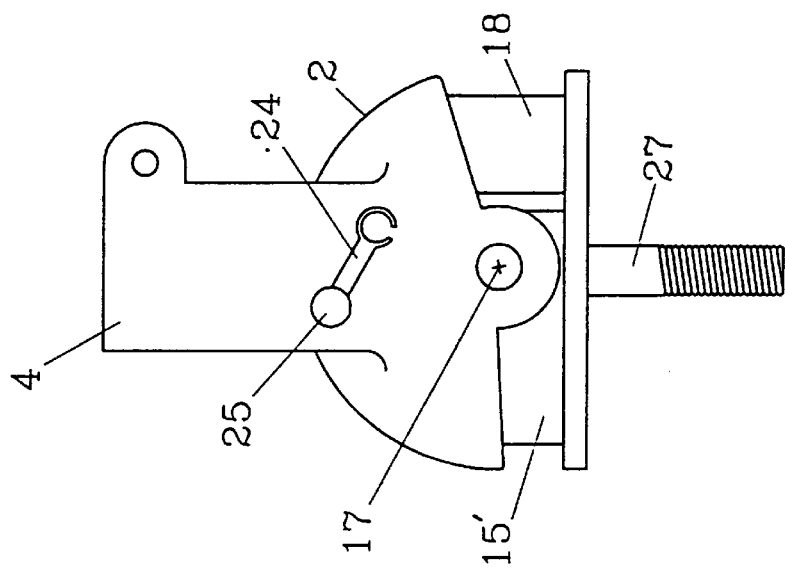
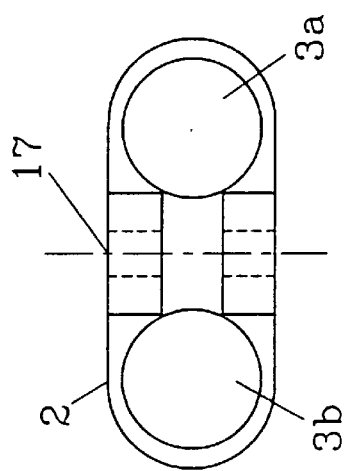
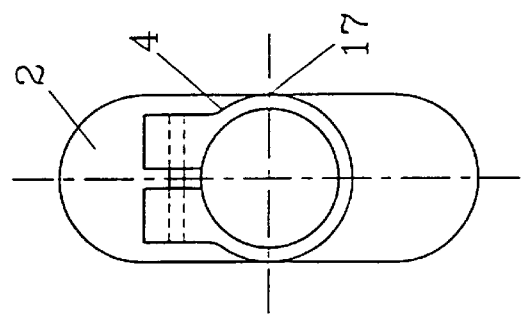
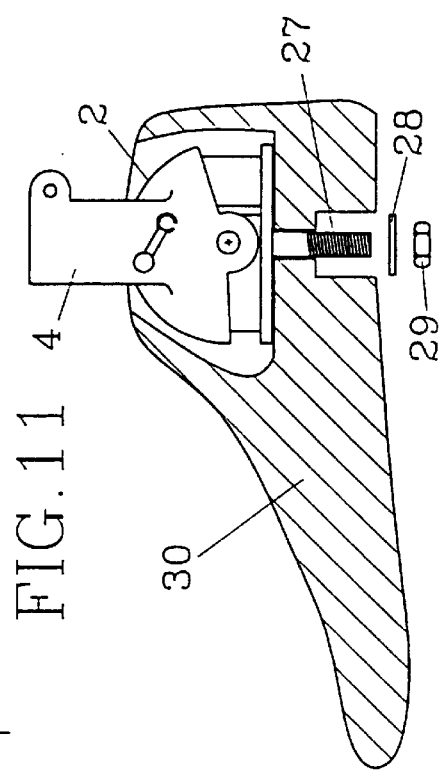

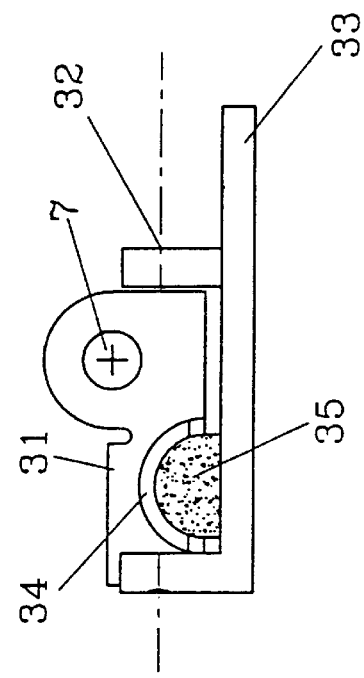
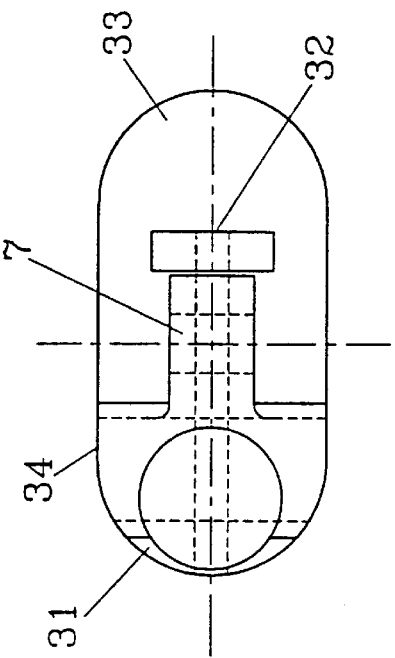
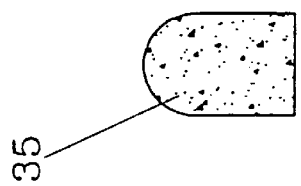
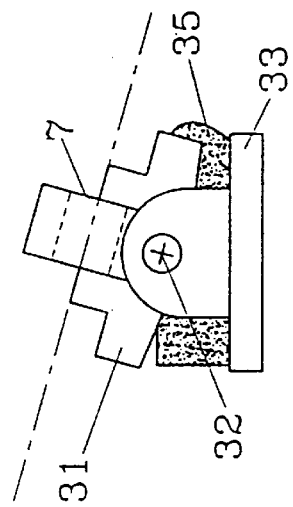
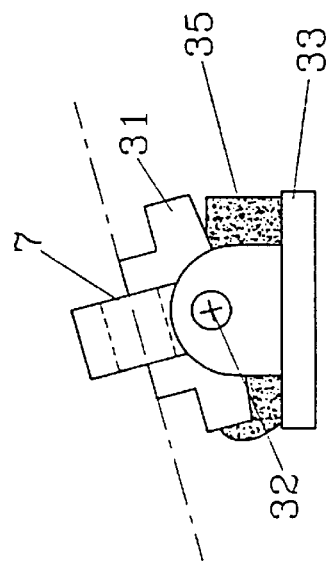

ADJUSTABLE PROSTHESIS JOINT

FIELD OF THE INVENTION

The present invention refers to an adjustable prosthesis joint, such as a prosthesis ankle or a prosthesis foot, of the type defined in the preamble of claim 1.

BACKGROUND OF THE INVENTION

From SE-A-9001184-2 is known an artificial foot, with which is obtained a rapid, step-less and smooth adjustment of the foot angle for a foot blade forming part of the foot, at the same time as the foot blade is resilient. The solution presented in that patent operates in a good manner, but incorporates a number of mechanical components, such as struts, rails, ball and nut mechanism, braking and arresting means, which together give the construction a rather large number of components, which make the foot according to the patent rather expensive and space-demanding.

The purpose of the present invention is to provide an adjustable prosthesis joint, such as a prosthesis foot or the like, which has the same high functionality as the artificial foot according to the above-mentioned patent, but which incorporates a smaller number of mechanical components and therefore can be made less space-demanding and less expensive to manufacture than the older solution, and this has been achieved in that the construction has been given the features defined in the characterizing part of claim 1.

Hereinafter the invention will be further described with reference to an embodiment schematically illustrated in the accompanying drawings.

BRIEF DESCRIPTION OF THE PREFERRED EMBODIMENTS

Figure 2:
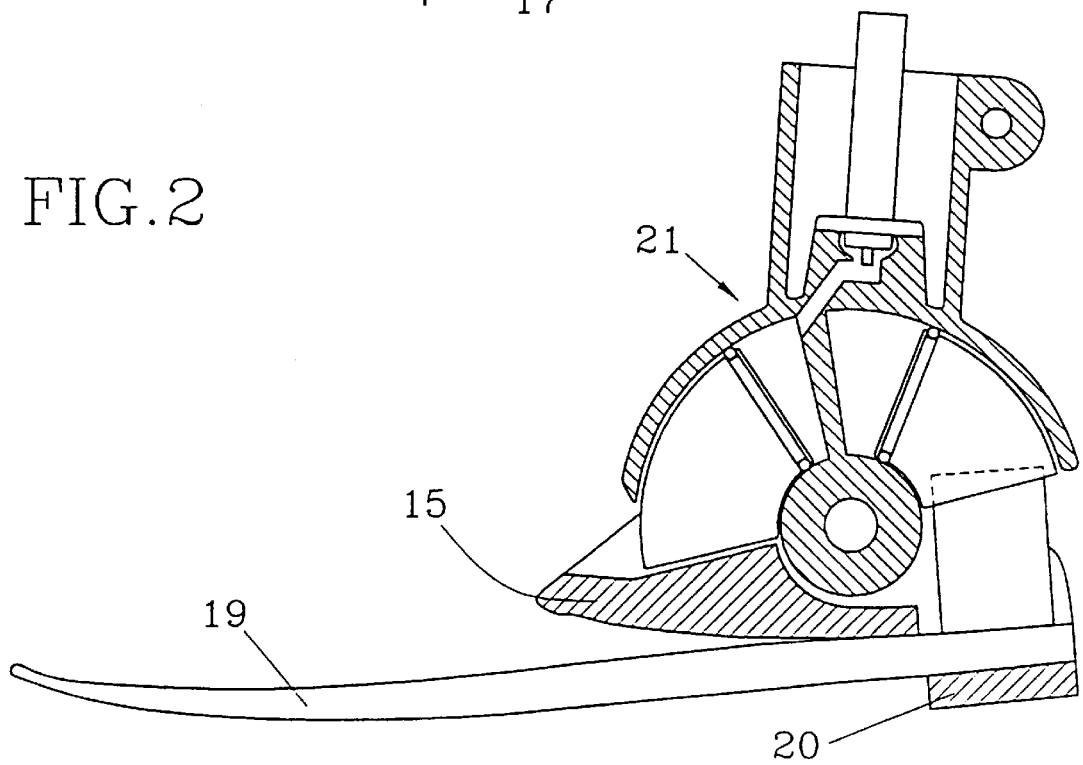
Figure 3:
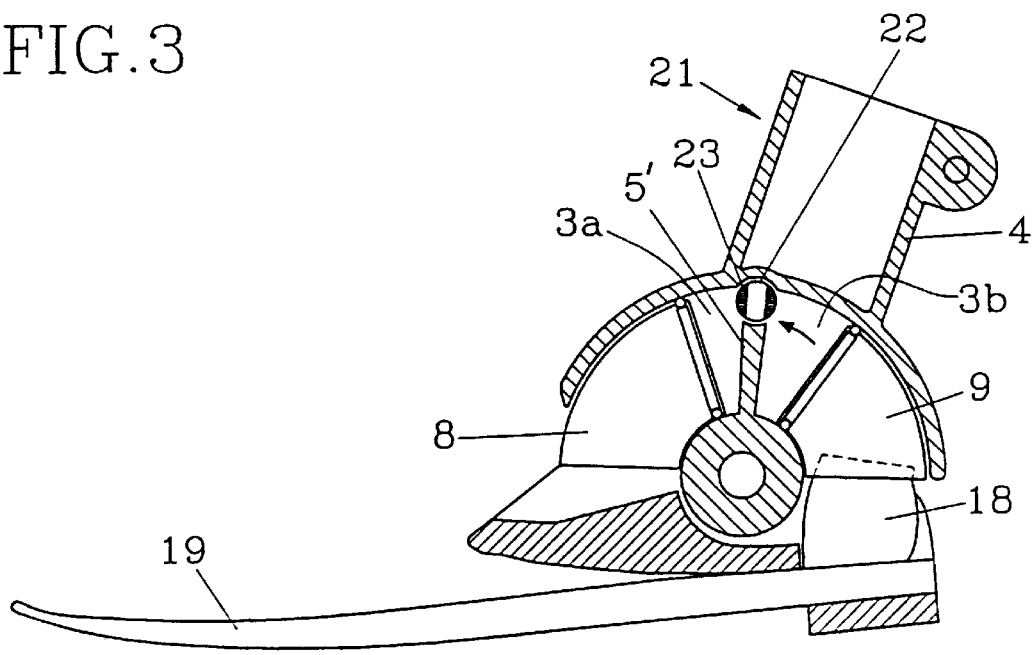
Figure 4:
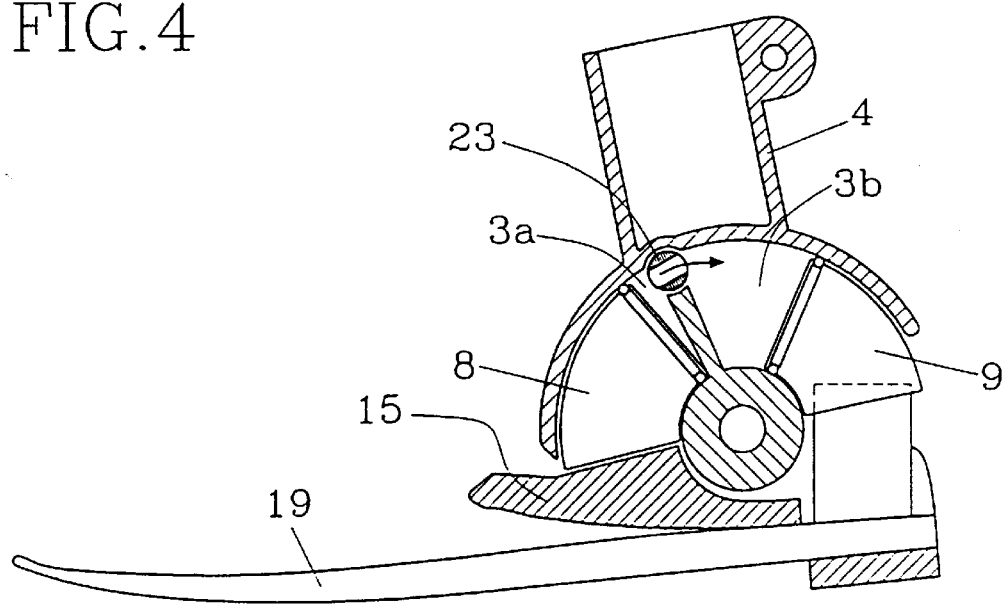
Figure 5:
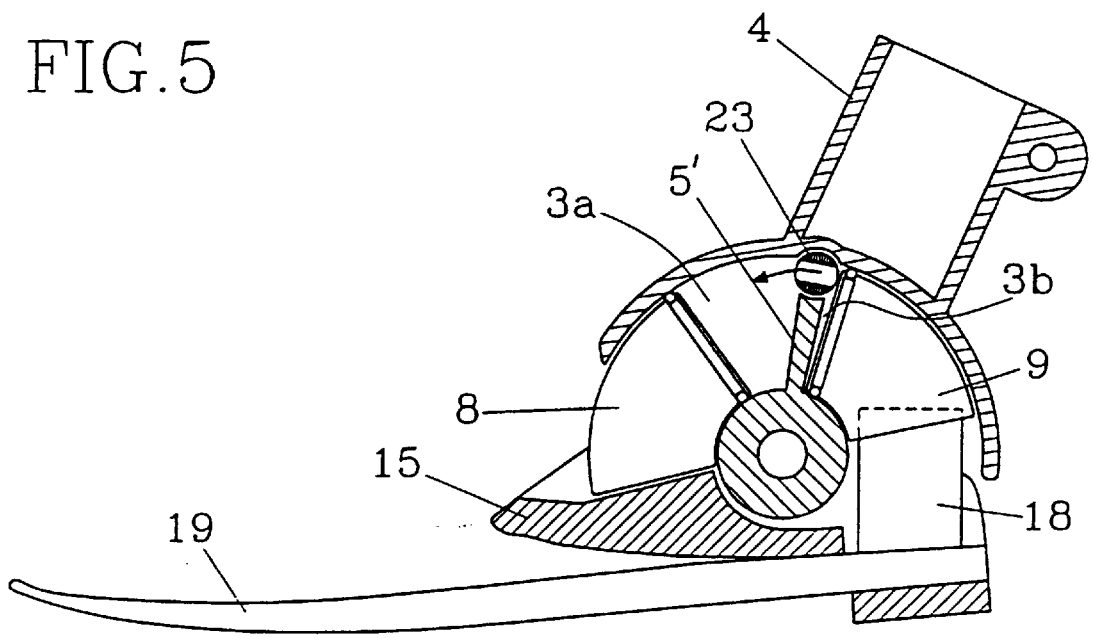
Figure 6:
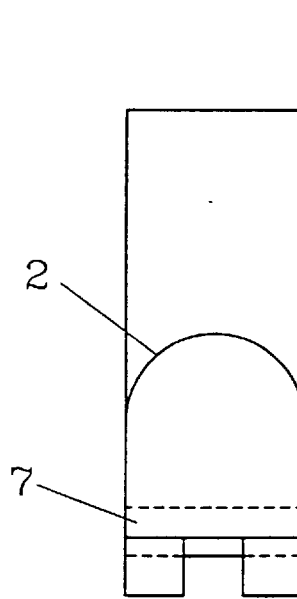
Figure 7:
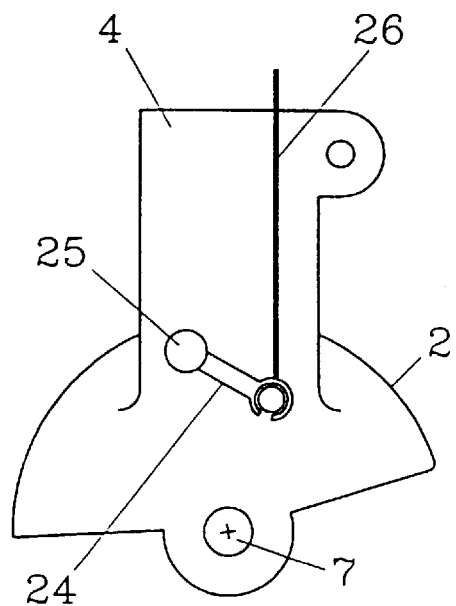

FIG. 1 shows in cross-section from the side an embodiment of an adjustable prosthesis ankle according to the invention, FIG. 2 is a corresponding view of a prosthesis foot according to the invention in a locked neutral position for a valve incorporated therein, and with load applied on the heel portion thereof, FIG. 3 shows a somewhat modified prosthesis foot according to the invention in a cross sectional view corresponding to FIG. 1, in a position bent maximally backwards, FIG. 4 is a corresponding view, which shows the foot prosthesis according to FIG. 3 in a position maximally bent forward and with the valve in open position, FIG. 5 is a view corresponding to FIG. 4 with open valve and in a position bent maximally backwards, FIG. 6 is an end view seen straight from the front of the valve housing according to FIG. 5, FIG. 7 shows the valve housing in side view, FIG. 8 illustrates the valve housing as seen straight from above, FIG. 9 is a view of the lower side of the valve housing in FIGS. 6–8, FIG. 10 shows an adjustable ankle joint according to the invention in side view, FIG. 11 shows partially in cross-section how the ankle joint according to FIG. 10 can be used together with one of a number of different, earlier known foot prosthesis, and FIGS. 12a–e illustrate schematically a further joint with which the prosthesis joint according to the invention can be built together for permitting lateral inclination.

In FIG. 1 is shown in cross-section an ankle joint prosthesis 1 according to the invention, which incorporates a housing 2 in the form of a substantially cylindrical, cross-sectionally circularly curved chamber 3 with a substantially straight socket 4 projecting essentially radially from the curved envelope surface thereof, which socket is intended to be attached to a not shown lower bone portion in a not further shown, e.g. conventional manner. In the middle portion of the cylindrical, curved chamber 3 there is provided a fixed, substantially radial intermediate wall 5, which subdivides the chamber 3 into two substantially equally big, circularly curved, partially circular cylinders 3a, 3b and which is connected to a hub 6 with a rotational axis coinciding with the axis of curvature 7 of the cylinders. In each one of those two cylinders 3a, 3b there are provided a piston 8, 9 each, which are curved in a manner corresponding to that of the cylinder, which pistons 8, 9 are interconnected in such a manner, that they form a continuous pair of pistons with a constant mutual spacing. The pistons are sealed off against the cylinder walls with conventional sealing arrangements 10, e.g. O sealing rings provided in grooves.

In the embodiment shown in FIG. 1, the intermediate wall between the chamber 3 and the attachment socket 4 is designed as a valve housing 11 with a first channel 12 opening in one of the cylinders 3a in the chamber 3, and a second channel, not visible in the figure, which opens in the second chamber 3b. In the valve housing 11 there is provided a rotatably arranged valve body 13, which in the position illustrated is open and therefor permits free communication between the two cylinders 3a, 3b. The valve body 13 can be turned by means of an operating means 14, e.g. a turning lever, in the example shown arranged through the attachment cylinder. Connected to the ankle prosthesis 1 according to the figure is a foot plate 15 rotatably arranged about the hub 6, and which in the neutral position shown has an upwardly facing surface 16 in contact with one of the pistons 8. The foot plate 15 in turn in this embodiment is connected to a heel plate 17, which supports a dampening body 18 of a flexibly compressible material, which is in contact with the other piston 9.

By the fact that the free space between each piston 8, 9 and the opposed surface of the intermediate wall 5 enclose an appropriate flow medium, is it possible with an appropriate dimensioning of the channels to cause such a dampening of the flow of flow medium between the different cylinders 3a, 3b in the open position of the valve body 13, that the attachment socket 4 very easily can be angularly adjusted to a desired degree in relation to an associated foot plate or a foot blade.

By using as a flow medium a visco-elastic mass, e.g. a boron-siloxan-elastomer, it is obtained a number of advantages in this connection, as the visco-elastic mass does not have high requirements for sealing accuracy, This means that the manufacturing tolerances for the cooperating sealing surfaces can be reduced, which contributes to a less expensive manufacturing. As a visco-elastic mass furthermore acts thus that it provides a bigger resistance to flow at more rapid movement it is possible to reduce the accuracy at manufacture of flow channels, valve housing and valve. In spite of theis, the invention is not limited to use of such visco-elastic masses as flow medium, but also common hydraulic oils can be used, whereby however the demands on manufacturing tolerances are increased.

In FIG. 2 is shown in a view corresponding to FIG. 1 the invention construed as a prosthetic foot 21, whereby the only difference as compared to the ankle joint prosthesis 1 according to FIG. 1, is that the foot plate 15 is connected to a foot blade 19 having a heel 20. The foot blade is earlier known and can preferably be a sheet made of carbon fibre material or the like. The flexibility thereof makes the foot blade 19 bend at walking to contact against the curvature of the lower surface of the foot plate 15.

In FIG. 3 is shown a modified embodiment of the prosthetic foot according to FIG. 2, whereby details in the two embodiments, which completely correspond to each other have been given the same reference numerals. The prosthetic foot 21 thus in this case has an intermediate wall 5', which separates the two chamber cylinders 3a, 3b, which houses the pistons 8, 9, said intermediate wall 5' being designed with a seating 22 for a rotatable valve body 23. In FIG. 3 the valve body 23 is in closed position, and maintains thereby the foot angle constant, which is normal at walking. In the figure is illustrated treading down on the heel, whereby the dampening body 18 is compressed such as can be seen. When the heel portion at walking motion is relieved from load, the dampening body 18 will again expand to initial size.

When it is needed to alter the foot angle, e.g. in connection with certain sports activities, when changing between shoes of different heel heights, etcetera, the valve body 23 as shown in FIG. 4, is opened and the flow medium in the communicating cylinders 3a, 3b can flow between the two cylinders. When applying a pressure on the attachment socket 4 in either inclination, the two pistons 8 and 9 situated at a constant mutual distance will move in relation to the intermediate wall 5', whereby the inclination of the attachment cylinder 4 in relation to the foot blade will be altered. Hereby the volume of flow medium will increase on one side of the intermediate wall 5', whereas it is reduced to a corresponding degree on the other side of the intermediate wall. When the valve body 23 thereupon is shifted to closed position, (see FIG. 3), the prosthetic foot will have taken up a new, arrested angular position relative to the foot blade.

In FIG. 4 is shown this altered angular position in position leaning forward to a maximum, but as the valve body 23 can be opened and closed anywhere along the path of movement it is possible to provide a completely stepless adjustment.

In FIG. 5 is shown in a corresponding manner how the attachment socket 4, when the valve body 23 is open, has been moved to a maximum rearward leaning position, whereby the piston 8 situated closest to the foot plate 15, engages the foot plate 15, just as in the position according to FIG. 4. In this maximally rearwardly leaning angular position, the dampening block 18 is still not compressed, whereas the space between the forward piston 8 and the intermediate wall 5' is the maximum space at the same time as the space between the rearward piston 9 and the intermediate wall 5' has its smallest size.

FIG. 6 shows in a planar front view the prosthesis joint according to the invention, with its housing 2, the attachment socket 4 and the curvature axis 7 of the hub.

FIG. 7 shows a planar side view of the housing 2 with its attachment socket 4 and the axis of curvature 7 thereof, and a possible arrangement for maneuvering the valve of the prosthesis joint, whereby this arrangement incorporates a lever 24, with a shaft 25 rotatably supported in the housing, which shaft is adapted to transfer the rotational movement of the lever to the valve body 23, and the free side of which can be connected to a maneuvering cable 26, which can be operated by the bearer of the prosthesis in that this person pulls the cable and thereby opens the valve when an angular adjustment is desired. A not shown spring is preferably arranged to return the valve to closed position when the pulling force in the cable ceases.

In FIG. 8 is shown the housing of the prosthesis joint in a planar view from above, and in FIG. 9 the same is shown in a planar view from underneath.

In FIG. 10 is shown in side view an embodiment of a prosthesis ankle, which is somewhat modified as compared to the prosthesis ankle according to FIG. 1. In this case the very prosthesis joint corresponds e.g. to the embodiment according to the prosthesis foot according to FIG. 3, whereas it on the other hand lacks a foot blade as well as a foot plate 15. The prosthesis ankle according to this embodiment is instead provided with a bottom member 15', which forms a counter surface for the forward piston.

This bottom member 15' is provided with a bolt 27 fitted thereto.

Such as schematically shown in FIG. 11, this prosthesis ankle may in a simple manner be used together with artificial foots already available on the market, in that they by means of a washer 28 and a nut 29 can be attached in a recess in the artificial foot 30, such as illustrated.

In FIGS. 12a–e is schematically illustrated how the prosthesis joint according to the invention can be built together with a second joint axis, provided substantially at right angle to the joint axis of the prosthesis joint according to the invention. When using the prosthesis joint as a foot prosthesis in this manner it is obtained a possibility also to incline the foot joint laterally. In FIG. 12a thus it is shown in a view straight from the front (or straight from the rear side) the rotational axis 7 at the prosthesis joint according to the invention, whereby the supporting bracket 31 for this rotational axis 7 is pivotably supported about a pivot journal 32, which extends substantially perpendicularly to the rotational axis 7. In this figure is shown how the joint can be inclined laterally about the pivot journal 32, and in FIG. 12b is illustrated the corresponding inclination in the opposite direction. In this manner it is possible well to adjust a foot joint angularly, such as e.g. corresponds to normal inclination of the foot joint when the feet are positioned wide apart from each other.

In FIG. 12c is shown the supporting bracket 31 and the pivot journal 32 from the side and from this view it also can be seen how a recess 34 is provided between the supporting bracket 31 and a base plate 33, in which recess is positioned a dampening block 35, e.g. made from polyurethane. Such dampening blocks, which are shown in FIG. 12d are inserted from each side of the recess 34 and dampen under compression lateral swinging motions, as can be seen from FIGS. 12a and 12b.

In FIG. 12e is shown the further joint in a view from above.

The invention is not limited to the embodiments shown and described in connection thereto, but modifications are possible within the scope of the accompanying claims.

What is claimed is:

1. An adjustable prosthesis joint to set the angular relation between an attachment socket for connecting the joint to a cooperating body member and a prosthesis detail, the prosthesis joint comprising:

a housing;

a chamber disposed in the housing;

an intermediate wall fixed within the chamber to subdivide the chamber into at least two communicating chamber portions;

an adjustable valve provided in a valve housing in connection to the wall, wherein the adjustable valve is movable between a closed position and an open position;

a flow medium to communicate between the chamber portions through the valve;

at least two pistons wherein each piston is movably disposed in one of the two chamber portions and the pistons are interconnected to and are adapted to be uniformly displaced in relation to the wall under flow of the flow medium through the valve in the open position between the chambers.

2. The adjustable prosthesis joint according to claim 1 further comprising a means to attach the joint to an artificial foot.

3. The adjustable prosthesis joint according to claim 1 wherein the position of the pistons is secured relative to the wall when the valve is in the closed position.

4. The adjustable prosthesis joint according to claim 1 wherein the cross-section of the chamber is curved so that the wall subdivides the chamber into two cylindrical curved chamber portions.

* * * * *